United States Patent [19]

Heyden

[11] Patent Number: 4,963,137
[45] Date of Patent: Oct. 16, 1990

[54] DEVICE FOR URINE DRAINAGE

[76] Inventor: Eugene L. Heyden, S. 627 Bernard, #8, Spokane, Wash. 99204

[21] Appl. No.: 312,386

[22] Filed: Feb. 17, 1989

Related U.S. Application Data

[63] Continuation of Ser. No. 70,078, Jul. 6, 1987, abandoned.

[51] Int. Cl.$^5$ ............................................. A61F 5/44
[52] U.S. Cl. ................................................. 604/349
[58] Field of Search ................ 604/317, 318, 349–353

[56] References Cited

U.S. PATENT DOCUMENTS

| | | |
|---|---|---|
| 2,789,560 | 4/1957 | Weimer . |
| 3,403,682 | 10/1968 | McDonell . |
| 3,648,700 | 3/1972 | Warner . |
| 3,739,783 | 6/1973 | Broerman ........................... 604/349 |
| 3,788,324 | 1/1974 | Lim . |
| 3,998,228 | 12/1976 | Poidomani ........................ 604/351 |
| 4,202,335 | 5/1980 | Gold . |
| 4,284,079 | 8/1981 | Adair . |
| 4,337,775 | 7/1982 | Cook et al. . |
| 4,500,314 | 2/1985 | Brendling ........................... 604/349 |
| 4,540,409 | 9/1985 | Nystrom et al. ................... 604/349 |
| 4,640,688 | 2/1987 | Hauser ............................... 604/352 |

FOREIGN PATENT DOCUMENTS 0123661 10/1984 European Pat. Off. ............ 604/349

Primary Examiner—Stephen C. Pellegrino

[57] ABSTRACT

An external catheter for use with male patients. The catheter is constructed of a resilient material such as a latex, and is characterized by a rearward portion adapted to loosely receive the penis, adhesively attach thereto, and fittingly mold about the same to effect a liquid-tight seal.

14 Claims, 2 Drawing Sheets

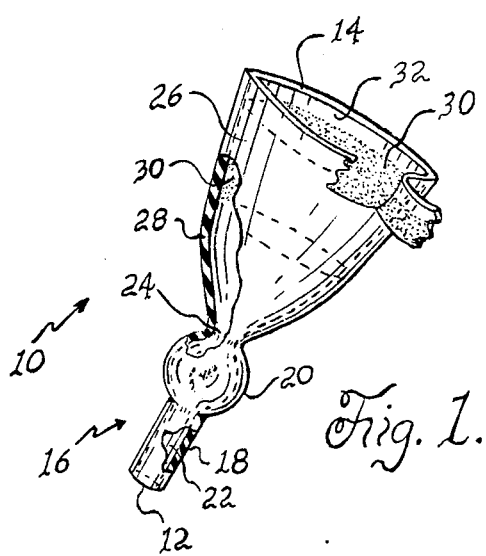
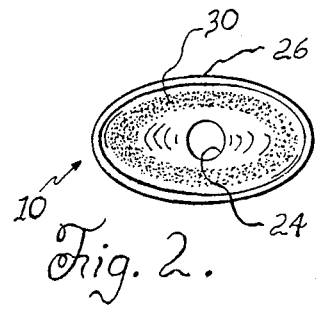
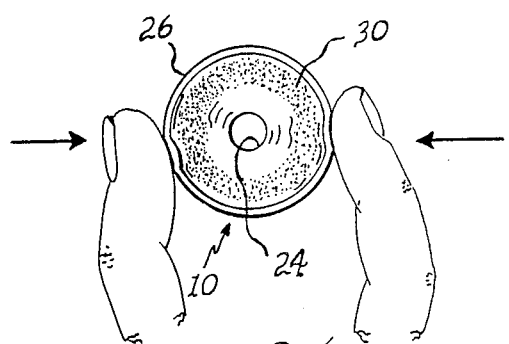
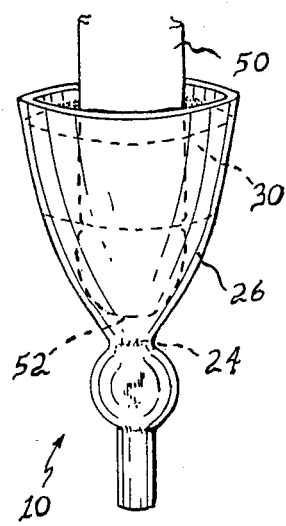
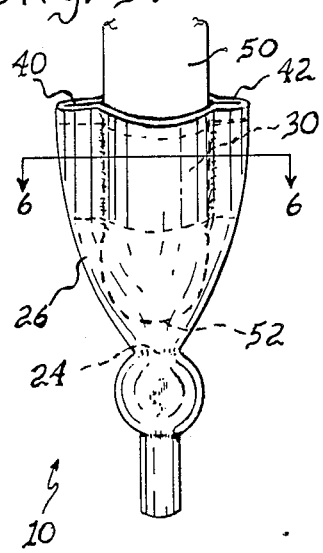
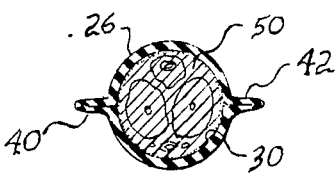
Fig. 1.
Fig. 2.
Fig. 3.
Fig. 4.
Fig. 5.
Fig. 6.

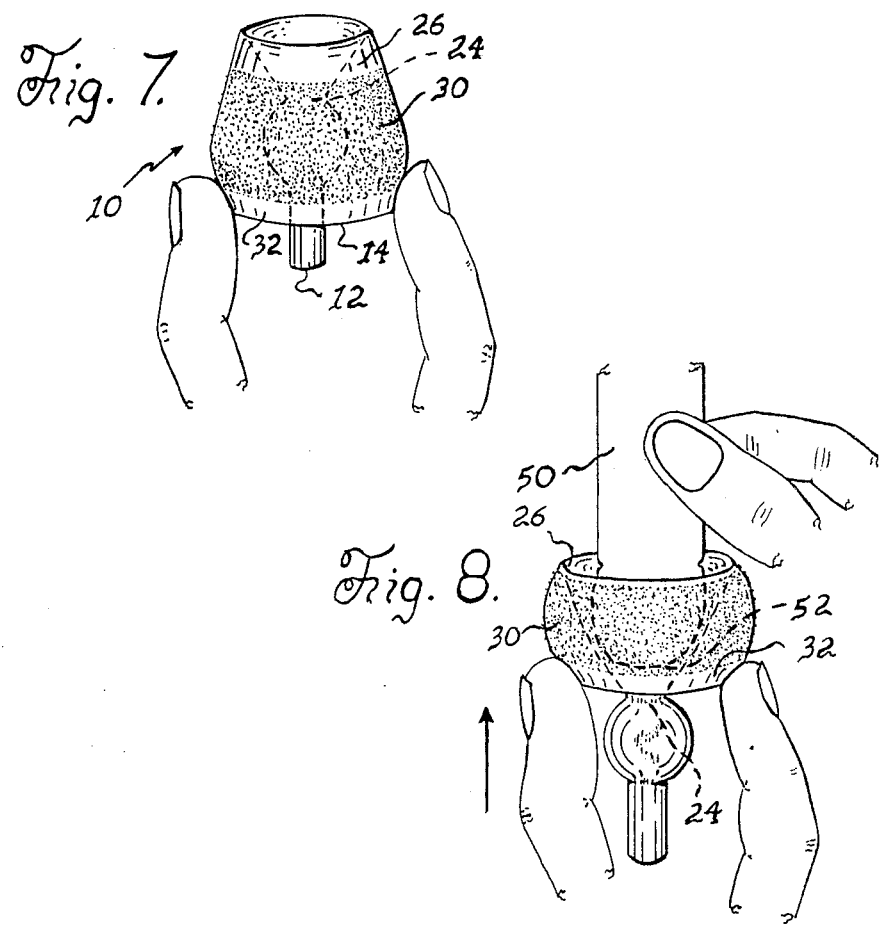

4,963,137

DEVICE FOR URINE DRAINAGE

CROSS REFERENCE TO RELATED APPLICATION

This application is a continuation of Ser. No. 070,078, filed Jul. 6, 1987, and now abandoned.

BACKGROUND OF THE INVENTION

This invention relates to external catheters for use with male patients, and represents an alternative to the condom-type of external catheter.

It is commonplace in a variety of clinical situations for patients to lose control of the discharge of urine. It is generally preferably to avoid transurethral catheterization of the uninary bladder as infection, discomfort, or internal injury can result. Accordingly, a condom catheter is often employed as an alternative to an invasive catheterization of the male patient.

The condom catheter generally comprises an elongated, circularly tubular sheath of one-piece construction having a forward portion defining a fluid passage, an intermediately-positioned conical or cup-shaped mid-portion providing a forward discharge opening in communication with the fluid passage, and a thin-walled rearward portion adapted for extending over the shaft of the penis. In catheters of this type, the rearward portion is prepared in an initial rolled up attitude to reside at the edge of the catheter's mid-portion, and is manually unrolled over the shaft of the penis during the application procedure. Also in catheters of this type, the rearward portion may have an adhesive substance on its inner wall surface to adhesively engage the penis and to effect a liquid-tight seal. And, the forward portion of the device may present a dilation at the base of its mid-portion which serves as a surge chamber and an anti-kink mechanism.

To function as intended, it is desirable to place and maintain the free end of the penis in near approximation to the forward discharge opening of the condom catheter. When the free end of the penis is maintained in such a position, a twisting, collapsing, or kinking of the catheter, to a degree which restricts the outflow of urine or contributes to an ill-fitting of the device, is largely prevented.

Unfortunately, improper positioning and poor fit are common problems associated with the condom catheter. Often encountered when applying the device are problems which occur when its rearward portion is unrolled over the shaft of the penis. It has been observed that the act of unrolling the rearward portion of the catheter tends to push the free end of the penis away from the forward discharge opening and out of a proper position within the mid-portion of the catheter, contributing to an improper fit of the device upon the penis. It has also been observed that the relative looseness of the penile skin tends to cause the same to be pushed ahead of the condom roll as the rearward portion of the catheter is unrolled, displacing the penile skin rearwardly away from a normal, relaxed position. In this eventuality, after the catheter is unrolled the penile skin will then return to a relaxed state and cause the free end of the penis to displace and withdraw from the intended position within the mid-portion of the catheter, leading to the aformentioned problems associated with an improper positioning and fit of the device.

Another disadvantage of the condom catheter that may be pointed out is the need for more than one size to be provided in order to adequately serve the various size requirement needs of the male patient community. Often it is difficult to determine, without trial and error, which of the available sizes is suitable for the individual need of the patient. And, even with a trial and error approach to determine the size of catheter most appropriate for a given patient, the catheter chosen may still be of a size that is too small or too large for a proper fit and function. Further, it is obvious that it is less expensive to manfacture a one-size-fits-all product than to manufacture a product that come in an assortment of sizes.

In view of the foregoing, it is one object of the present invention to provide an external catheter construction which will fulfill the functional intent of the condom catheter but will not push the free end of the penis away from a forward discharge opening or push the penile skin ahead of a catheter roll during the application procedure.

It is a further object of the present invention to provide an external catheter that can be constructed such that one size substantially meets the individual size requirements of the male patient community.

These and other objects will become readily apparent as the summary and detailed description of the invention are studied in connection with the attending drawing.

SUMMARY OF THE INVENTION

With the above considerations in mind, the present invention provides an external catheter of one-piece construction, formed of a latex or similar material, and generally tubular in nature. The device includes a forward portion defining a fluid passage, and an opposing rearward portion presenting a forward discharge opening in fluid communication with said fluid passage. The rearward portion is dimensioned to loosely receive the penis, is substantially shape-retaining, and, having a band of adhesive substance portionally located on its inner wall surface, is adapted to adhesively engage the penis and fittingly mold about the same as portions of the inner wall surface of the rearward portion are adhesively joined at the sides of the penis and are joined to the penis itself. Further demonstrated in the preferred embodiment is a rearward portion that is conical or cup-shaped in its progression away from the forward portion of the catheter, as well as being generally elliptical as it surrounds the longitudinal axis of the catheter. The elliptical nature of the rearward portion of the catheter presents, when in a relaxed state, opposing sides that reside relatively close to each other and opposing sides that are elliptically most distant from each other. By such an arrangement, it is intended that a degree of restriction to a free reception of the penis be presented by the catheter. It is also intended, however, that the elliptically most distant sides of the catheter's rearward portion be urged inwardly during the application procedure to widen said rearward portion, in order to freely receive the penis and allow the free end thereof to reside near the forward discharge opening of the device. After an insertion of the penis within the catheter is performed, the catheter's rearward portion is released to allow the catheter wall to resiliently move inward and form an initial adhesive attachment to the penis. The initial adhesive attachment acts to maintain the penis in proper position until and while the remainder of the rearward portion of the catheter is fittingly molded about the penis to sealingly engage the same. An alternative application procedure is also contemplated, and includes an inversion of the rearward portion of the catheter followed by its extension over the penis.

BRIEF DESCRIPTION OF THE DRAWING

The invention can best be understood in conjunction with the accompanying drawing in which:

FIG. 1 is a perspective view of the catheter in the preferred embodiment, having portions thereof cut away or otherwise adapted for illustrative purposes;

FIG. 2 is a top view of the catheter of FIG. 1;

FIG. 3 illustrates an inward urging of the rearward portion of the catheter to effect a generally circular deformation thereof to allow the insertion of the penis therewithin;

FIGS. 4, 5, and 6 illustrate the catheter during and after the preferred procedure for applying the catheter to the penis; and FIGS. 7 and 8 represent, in part, an alternative procedure for applying the catheter to the penis.

DETAILED DESCRIPTION OF THE PREFERRED EMBODIMENT

With particular reference to FIGS. 1 and 2 of the drawing, the invention in the preferred embodiment comprises an external catheter 10 of one-piece construction including a tubular forward portion 16 and associating forward edge 12 in axial alignment with an opposing, generally conical or cup-shaped rearward portion 26 and associating rearward edge 14. During its intended use as a device for urine drainage, the forward portion 16 of the catheter is connected to a drainage tube for the transfer of urine to a drainage receptacle (not shown), while the rearward portion 26 is adhesively attached to the penis and is fittingly molded about the same, as will be discussed more fully in connection with the discussion of FIGS. 3 through 6. The rearward portion of the catheter is adapted in size to loosely receive and to loosely accommodate what would be a relatively large penis, and thus is also adapted to accommodate a wide range of penis sizes ranging from small to large. Though a one-size-fits-all scheme is contemplated, it would be well within the practice of the present invention to provide, for example, one size intended for a small to medium size penis and another size intended for a medium to large size penis.

Continuing with the description of the invention in the preferred embodiment, the external catheter 10 is constructed of a resilient material such as a latex, presents a wall 28 of substantially uniform thickness between inner and outer wall surfaces that is continuous about the longitudinal axis of the catheter, and has a wall thickness that cooperates with the degree of resiliency of the material used in its construction to define a substantially shape-retaining, yet readily deformable structure. It is to be understood that each portion of the device may be considered as having itself a wall, even though the device, in essence, presents only one wall beginning and ending at the edges of the device. The wall thickness of the rearward portion of the catheter may be on the order of 0.025 to 0.050 of an inch, while the forward portion may be of an equal or greater wall thickness. Preferred in the construction of the device is a dip molding process of manufacture.

An optional feature incorporated in the catheter 10 is a dilation in its forward portion 16 which defines a surge chamber 20 and a non-kinking area for flexion. A surge chamber, such as herein illustrated and briefly described, is well known to the art.

Proceeding further in the discussion of the invention in the preferred embodiment, the forward portion 16 of the catheter is circularly tubular in its forward part 18, and defines a central fluid passage 22 extending from the forward edge 12 of the catheter to a forward discharge opening 24 defined collectively by the surge chamber 20 and the catheter's rearward portion 26. The forward discharge opening 24, common to both forward and rearward portions of the catheter allows fluid communication between central fluid passage and the rearward portion of the device.

In member relation to the catheter is a continuous adhesive band 30 residing on the inner wall surface of its rearward portion 26. The adhesive band 30 comprises a thin layer of medically-approved adhesive substance which is suitable for application to latex and the like and is suitable for the purposes of the present invention. Though in the practice of the present invention the adhesive substance may reside on the entire inner wall surface of the rearward portion of the catheter (or even the inner wall surface of the entire catheter for that matter), it is preferred that the adhesive band 30 be spaced a distance both below the rearward edge 14 of the catheter and above the forward discharge opening 24 so that the adhesive band will avoid adhesive contact with the more delicate tissue area of the urethral meatus and glands region of the penis (a consideration particularly relevent to the circumsized patients) and will define a non-adherent band 32 between the adhesive band 30 and the rearward edge 14 of the catheter. The non-adherent band 32, provided in effect by the adsence of adhesive material on this portion of the catheter's inner wall surface, serves a later-identified purpose during the removal of the catheter from the penis.

FIGS. 1 through 3, taken together, illustrate other features of the present invention in the preferred embodiment. Specifically, the rearward portion 26 of the catheter progresses and progressively enlarges away from the forward discharge opening 24 in a manner that causes the wall thereof to resemble a cone-shaped or conical structure, while, at the same time, said rearward portion 26 is constructed to elliptically surround the longiltudinal axis of the device. As is clearly shown in FIG. 2, the elliptical nature of this portion of the catheter presents opposing sides that reside relatively close or adjacent to each other and opposing sides which are elliptically most distant from each other when the rearward portion of the catheter is in a relaxed state. This arrangement contemplates a width between the relatively close sides of the catheter's rearward portion which will normally interfere with a free reception of the penis therewithin. It is intended, however, that the elliptically most distant sides of this portion of the catheter be urged inwardly (FIG. 3) to widen the distance between said sides in preparation for a non-restrictive reception of the penis. Also intended is a release of the rearward portion of the catheter against opposing sides of the penis after its insertion therein. Accordingly, when released, the rearward portion will resiliently return to its relaxed state, lightly compress against the penis, and form an intial adhesive contact therewith which will maintain the penis in the position in which it was placed within the catheter. Alternatively, however, the practice of the invention may include a catheter having a rearward portion which is of circular configuration about the central axis of the catheter and will have, in the relaxed state, a combined appearance of FIGS. 1 and 3. In a catheter of this configuration, opposing sides of its rearward portion may be manually compressed after receiving the penis in order to initiate adhesive contact therewith.

Turning now to FIGS. 3 through 6, the placement procedure, and completion of this procedure, is illustrated. The placement of the catheter upon the penis may be performed by an attendent or by the patient himself. One method of applying the catheter 10 involves an inward urging of the eliptically most distant sides of the catheter's rearward portion 26 by thumb and forefinger manipulation (FIG. 3), a placing of the free end 52 of the penis 50 in close space-relation to the forward discharge opening 24 of the catheter followed by the act of releasing the rearward portion 26 of the catheter upon the penis for initial adhesive contact (FIG. 4), and a molding and an adhesive securing of said rearward portion 26 about and to the penis 50 to effect a liquid-tight seal between the penis and inner wall surface of the catheter's rearward portion (FIGS. 5 and 6). The catheter may be fittingly molded about the penis by starting from the midline areas of initial adhesive contact and by manually pressing the rearward portion against and surroundly about the penis in a fashion whereby the excess of the rearward portion of the catheter not used to surround the penis will form, when pressed together, bilaterally projecting adhesive-to-adhesive wall approximations 40 and 42 of longitudinal extent and comprising adhesively approximated longitudinal sections of said rearward portion. When the catheter is fittingly molded about the penis and adhesively secured thereto as intended, the adhesive substance, in cooperation with the flexibility of the rearward portion of the catheter and the relative looseness of the penile skin, will act to prevent the leakage of urine past the device in the areas of the performed wall approximations 40 and 42.

It can readily be appreciated that by releasing the rearward portion 26 of the catheter upon the penis 50, the initial adhesive contact between the adhesive band 30 and the penis 50 which follows will maintain the penis in an intended position while the rearward portion 26 of the catheter is formed about the penis to effect a liquid-tight seal therebetween. It can also be appreciated that the rearward portion of the catheter will, when correctly applied to the penis, adapt to individual size requirements for the creation of a liquid-tight seal. It can further be appreciated that the application of the device upon the penis will not, as is common with the condom type of catheter, act to push the free end 52 of the penis away from the forward discharge opening 24 of the catheter nor act to rearwardly displace the penile skin away from the catheter by the unrolling action of a rearward portion. It should be noted that the catheter need not cover the entire length of the penis for a proper application and that, though highly preferred, the free end of the penis need not necessarily be in close approximation to the forward discharge opening, as the shape-retaining character of this portion of the catheter will help prevent a twisting or a collapsing thereof which would restrict the outflow of urine from the device.

Another method of manually applying the catheter to the penis is outlined by FIGS. 7 and 8. Whether constructed elliptically or circularly about the central axis of the catheter, the generally conical or cup-shaped nature of its rearward portion 26, in cooperation with the resiliency of the material used in the catheter's construction, allows the rearward portion of the catheter to be easily inverted, into a self-maintained inverted stated with the rearward edge 14 of the catheter facing in the direction of the catheter's forward edge 12. According to this method of application, then, the inverted rearward portion 26 of the catheter 10 will outwardly expose the adhesive band 30, as shown in FIG. 7, and will prevent its contact with the penis when the penis is placed at or near the forward discharge opening 24. Subequent to the inversion of the rearward portion 26 of the catheter, the penis 50 is placed in axial alignment with the catheter and the free end 52 of the penis 50 is placed near or against the inner wall surface of the catheter in the area of the forward discharge opening 24, followed by an extension of this portion of the catheter in what may be called "roll-sock fashion" over the penis, as illustrated in FIG. 8. After the complete extension of the rearward portion of the catheter over the penis, the rearward portion is then fittingly molded about the penis and is adhesively attached thereto in the manner described in connection with FIGS. 3 through 6. The non-adherent band 32 presents a suitable non-sticky holding area during this alternative placement procedure.

Recalling the location and provision of the non-adherent band 32, it will be seen that the rearward portion of the catheter above the adhesive band 30 will freely separate from the penis 50. The removal of the catheter may be accomplished by grasping this portion of the catheter on opposing sides and at locations distant from the wall approximations with a thumb and forefinger grasp, followed by a slow, steady pulling action of the catheter away from the penis to effect an adhesive separation of the catheter from the penis and to effect a separation of wall approximations 40 and 42.

In conclusion, it should be pointed out that the shape-retaining nature of the catheter will ordinarily prevent an unintended adhesive bonding between portions of the adhesive band unless the catheter is sufficiently compressed. To prevent this from happening during shipping and storage however, it would be appropriate to package the device in a rigid container, such as a box or a clam shell plastic container, as opposed to the use of a flexible-walled bag.

Though presented in its preferred embodiment, it is to be understood that the present invention may be practiced according to variations from that which is described herein and/or by the substitution of equivalents.

What is claimed is:

1. A device for urine drainage which is moldably conformable about a penis and adhesively securable thereto, comprising:
   a generally tubular sheath of one-piece construction and of flexible material presenting a wall formed continuously about a longitudinal axis and including
   a forward portion of longitudinal extent internally defining a fluid passage means, and
   a substantially shape-retaining rearward portion of longitudinal extent emerging from said forward portion and generally progressively enlarging in circumference substantially its entire length as it progresses longitudinally away from an internally defined forward discharge opening means common to both forward and rearward portions of said sheath, said rearward portion having an inner wall surface and existing in fluid communication with said fluid passage means by means of said forward discharge opening; and adhesive means located on a substantial amount of the inner wall surface of said rearward portion, whereby said rearward portion may adhesively engage the penis and adhesively join together portions of said inner wall surface in order to moldably conform about the penis wherein said rearward portion is of a dimension to loosely receive the penis.

2. The device of claim 1, wherein said rearward portion is generally conical in its longitudinal progression away from said forward discharge opening.

3. The device of claim 1, wherein said rearward portion is generally eliptical about said longitudinal axis when in a relaxed state so as to define elliptically most distant sides and elliptically most adjacent sides, whereupon, during the application of the sheath to a penis, the elliptically most distant sides of said rearward portion may be urged toward one another so as to outwardly urge the elliptically most adjacent sides of said rearward portion away from one another in order to allow the insertion of the penis within said sheath, and whereupon with a release of said rearward portion said sheath will at least partially return to its relaxed state and the elliptically most adjacent sides will adhesively engage the penis.

4. The device of claim 1, wherein said rearward portion is generally circular about said longitudinal axis when in a relaxed state, so that said rearward portion may be urged into an eliptical state in order to achieve an intial adhesive attachment to the 5. The device of claim 1, wherein said adhesive means comprises an adhesive substance layer located upon the inner wall surface of said rearward portion.

6. The device of claim 5, wherein said adhesive substance layer is substantially continuous about the longitudinal axis of said sheath and defines a substantially continuous band of adhesive located upon the inner wall surface of said rearward portion.

7. The device of claim 6, wherein said rearward portion continues toward a rearward edge defined by said sheath and opposed by said forward portion, and said band of adhesive is spaced a predetermined distance from said rearward edge whereby a non-adherent band means is defined between said rearward edge and said band of adhesive.

8. The device of claim 6, wherein said band of adhesive is spaced a predetermined distance from said forward portion.

9. The device of claim 1, wherein said rearward portion is of sufficient flexibility so as to allow for an inversion thereof prior to the application of said device on the penis.

10. The device of claim 1, wherein said forward portion includes an enlargement defining a surge chamber means residing in the vicinity of said rearward portion.

11. A method of applying a generally tubular external catheter of one-piece construction to a penis, wherein said external catheter has a flexible, substantially shape-retaining rearward portion presenting a wall which is continuous about a longitudinal axis and which is sized to accommodate said penis, wherein said rearward portion normally maintains both a generally conical and a generally eliptical configuration about a longitudinal axis when in a relaxed state, has opposing eliptically most distant sides and opposing eliptically most adjacent sides, and also has an adhesive means residing on a substantial amount of its inner wall surface, and wherein said rearward portion interferes with the reception of said penis when said rearward portion is in its relaxed state, said method including the manually performed steps of:

deforming said rearward portion by urging the eliptically most distant sides of said rearward portion toward said longitudinal axis a distance sufficient to outwardly urge the eliptically most adjacent sides of said rearward portion to a degree whereby said rearward portion will non-restrictively receive said penis;

placing said penis a substantial distance within said rearward portion;

releasing said rearward portion upon said penis so that the eliptically most adjacent sides of said rearward portion will adhesively engage portions of said penis; and adhesively joining adjacent longitudinal portions of the wall of said rearward portion in order to fittingly mold said rearward portion about said penis in order to effect a liquid-tight seal.

12. A method of applying an external catheter of one-piece construction to a penis wherein said external catheter is constructed about a longitudinal axis and defines a tubular and flexible forward portion of longitudinal extent defines a tubular and flexible rearward portion of longitudinal extent that emerges from said forward portion and generally progressively enlarges in circumference substantially its entire length as it progresses longitudinally away from an internally defined forward discharge opening common to both forward and rearward portions of said catheter, said rearward portion being of a dimension to loosely receive said penis, having a wall with an inner wall surface and having an adhesive substance located on substantial portions of said inner wall surface, having a rearward edge defined by said rearward portion and opposing said forward portion, and possessing a degree of flexibility that allows for an inversion thereof in order to achieve a substantially self-maintained inverted state, the method including the manually performed steps of:

inverting said rearward portion to effect a substantial degree of inversion in order to achieve said substantially self-maintained inverted state so that substantial portions of the inner wall surface of said rearward portion are outwardly exposed;

placing the free end of said penis in the vicinity of said forward discharge opening means and substantially in axial alignment with said external catheter;

extending said rearward portion over a substantial portion of said penis by urging said rearward portion out of said substantially self-retained inverted state and;

effecting at least one longitudinally extending projection of the wall of said rearward portion which extends radially outwardly from the longitudinal axis of said catheter, said longitudinally extending projection comprising adhesively joined longitudinal increase in their amount of projection as they progress towards said rearward edge.

13. A method of applying and adhesively-securing a flexible external catheter to a penis, wherein said external catheter has a substantially shape-retaining and generally conical rearward portion of longitudinal extent having a wall with an inner wall surface and a rearward edge opposing a tubular forward portion, wherein said rearward portion emerges and generally progressively enlarges substantially its entire length from an internally defined forward discharge opening common to said forward portion and said rearward portion, has an adhesive means residing on substantial portions of the inner surface of said rearward portion, and is of a dimension whereby said penis may be freely received thereby, said method comprising the manually performed steps of:

- positioning said rearward portion in front of the free end of said penis;
- effecting the inclusion of the free end of said penis a substantial distance within said rearward portion; and
- adhesively joining adjacent longitudinal portions of the wall of said rearward portion in order to fittingly mold said rearward portion about said penis in order to effect a liquid-tight seal whereby the joining forms at least one longitudinally extending projection of the wall of said rearward portion which extends radially outwardly from longitudinal axis of said external catheter and comprises joined longitudinal sections of the wall of said rearward portion which progressively increase in their amount of projection as they progress towards the rearward edge of said external catheter.

14. An arrangement for managing the discharge of urine from a penis member of a male, comprising:

- a generally tubular device of one-piece construction for the drainage of urine, said device having a forward portion of longitudinal extent connectable to a drainage tube means, a rearward portion of longitudinal extent emerging from said forward portion, and an internally defined forward discharge opening common to said forward portion and said rearward portion, said rearward portion generally progressively enlarging in circumference substantially its entire length as it progresses longitudinally away from said forward discharge opening and toward a rearward edge defined by said rearward portion and opposed by said forward portion, said rearward portion having a wall with an inner wall surface, being of sufficient flexibility to moldably conform about said penis member, and having an adhesive substance located on the inner wall surface of said rearward portion; and
- at least one longitudinally extending projection of the wall of said rearward portion which extends radially outwardly from the longitudinal axis of said device and comprises joined longitudinal sections of said rearward portion which progressively increase in their amount of projection as they progress towards said rearward edge.

* * * * *